United States Patent [19]

Bringman

[11] Patent Number: 4,959,457

[45] Date of Patent: Sep. 25, 1990

[54] ANTI-LYMPHOTOXIN

[75] Inventor: Timothy S. Bringman, Oakland, Calif.

[73] Assignee: Genentech, Inc., S. San Francisco, Calif.

[21] Appl. No.: 616,502

[22] Filed: May 31, 1984

[51] Int. Cl.[5] ...................... C07K 15/28; C07K 17/02; C07K 3/12; C08H 1/00

[52] U.S. Cl. .................................... 530/387; 530/389; 530/390; 530/391; 530/808; 530/412; 530/413; 530/813; 530/815; 424/1.1; 424/85.8; 435/70.21; 935/108; 436/547; 436/529; 436/531; 436/548; 525/541; 525/542

[58] Field of Search ........................ 260/112 B, 112 R; 435/68, 172, 240, 948; 424/85, 1.1, 85.8; 436/529, 547, 531, 548; 525/54.1, 54.2; 530/387, 389, 391, 808, 809, 810, 813, 815

[56] References Cited

U.S. PATENT DOCUMENTS

| | | | |
|---|---|---|---|
| 4,474,754 | 10/1984 | Shimizu et al. | 424/88 |
| 4,481,137 | 11/1984 | Ohnishi et al. | 260/112 R |
| 4,513,088 | 4/1985 | Levy et al. | 435/68 |
| 4,578,335 | 3/1986 | Urdadn et al. | 530/351 |

FOREIGN PATENT DOCUMENTS

| | | |
|---|---|---|
| 0087087 | 8/1983 | European Pat. Off. . |
| 2108528 | 4/1983 | United Kingdom . |

OTHER PUBLICATIONS

Sevier et al., *Clin. Chem.,* 27, 1981, pp. 1797–1806.
Mizel et al., *J. Immunol.,* 131, 1983, pp. 1834–1837.
Smith et al., *J. Immunol.,* 131, 1983, pp. 1810–1815.
Chisholm, High Technology, 1983, pp. 57–63.
Vass et al., (eds.), Fluorescein Hapten: An Immunological Probe, CRC Press 1984.
Goding (ed.), Monoclonal Artibodies Principles and Practice AP, 1986.
Bio Rad Chromato., Electrophoresis, Immunochem, Mol. Bio., HPLC 1986.
Servier et al., *Clin Chem.* 27(11) 1981, pp. 1797–1806 (Review Article).
Synthetic Adjuvants, Adam, 1985, ed., (p. 150).
Modern Approaches to Vaccines, Chanock et al., 1984, ed., p. 248.
CA. No. 23146, vol. 81, 1974, "Mechanism of Cytoxicity of Soluble Factors from Lymphocytes", Walker et al.
Harris et al., "The Human LT Serum X. The Initial Form . . . Classes", *J. Immunol,* vol. 126(6), 1981, pp. 2165–2170.
Fair et al., "Release of LT Molecules . . . in Vitro", *Mol. Immunol, vol. 16, 1979, pp. 185–192.*
Yamamato et al., "Pharbolmyristate Arebule. . . In Virto", *J. Biol. Resp. Modifiers,* vol. 3, 1984, pp. 76–87.
Human T Cell Hybridoma Producing Lymphokines, Kobayashi et al., *J. Immunol,* 128(6), 1982, p. 2714.
Continuous Cultures of Fused Cells Secreting Antibody of Predetermined Specificity, Kohler et al., *Nature,* 256(5517), 1975, p. 495.
S. Fazekas de St. Groth et al., "J. Imm. Methods" 35:1–21, (1980).
Osebold, J. JAVMA, 181(10):983–987, (1982).
Edelman, R. Rev. Infectious Dis., 2(3):370–383, (1980).
Yamamoto et al., "Cellular Immunology" 38:403–416, (1978).
Gately et al., "Cellular Immunology" 27: 82–93, (1976).
Hiserodt et al., "J. of Immunology" 119(2): 374–380, (Aug. 1977).
Zacharchuk et al., "P.N.A.S. U.S.A." 80: 6341–6345, (Oct. 1983).

(List continued on next page.)

*Primary Examiner*—Garnette D. Draper
*Attorney, Agent, or Firm*—Carolyn R. Adler; Max D. Hensley

[57] ABSTRACT

Antibody is provided which is capable of neutralizing the in vitro anti-neoplastic cellular activity of lymphotoxin. This antibody, which preferably is produced of monoclonal fusions, can be used in assays for lymphotoxin or for immunoaffinity purification of lymphotoxin.

4 Claims, 8 Drawing Sheets

OTHER PUBLICATIONS

Männel et al., "Infection and Immunity" 33(1): (Jul. 1981).

Wallach et al., DeMaeyer et al., Ed., "The Biology of the Interferon SYstem", pp. 293–302, (Pub. Sep. 1983).

Stone-Wolff et al., "J. Exp. Med." 159: 828–843, (Mar. 1984).

De Weck et al., Ed., "Biochemical Characterization of Lymphokines", pp. 279–312, (1980).

Ruddle et al., "Lymphokine Research" 2(1): 23–31, (1983).

Williamson et al., "P.N.A.S. U.S.A." 80: 5397–5401, (Sep. 1983).

Wright et al., "J. of Immunology" 126(4): 1516–1521, (Apr. 1981).

Papermaster et al., "Cancer" 45: 1248–1253, (1980).

Klostergaard et al., "Molecular Immunology" 18(12): 1049–1054, (1981).

Granger et al., "Lymphokine Research" 1(2): 45–49, (1982).

```
                                                                                      -30
                                                                      met thr pro pro glu
GAGGTTTATTGGGCCTCGGTCCTCCTGCACCTGCTGCCTGGATCCCCGGCCTGCCTGGGCCTGGGCCTTGGTTCTCCCC ATG ACA CCA CCT GAA
1                                                       50

                                         -20                                          -10
arg leu phe leu pro arg val cys gly thr thr leu his leu leu leu leu gly leu leu leu val leu leu pro
CGT CTC TTC CTC CCA AGG GTG TGT GGC ACC ACC CTA CAC CTC CTC CTT CTG GGG CTG CTG CTG GTT CTG CTG CCT
     100                                                                150

                1                                       10                                    20
gly ala gln gly Leu Pro Gly Val Gly Leu Thr Pro Ser Ala Ala Gln Thr Ala Arg Gln His Pro Lys Met His
GGG GCC CAG GGG CTC CCT GGT GTT GGC CTC ACA CCT TCA GCT GCC CAG ACT GCC CGT CAG CAC CCC AAG ATG CAT
                                         200

                                  30                                      40
Leu Ala His Ser Thr Leu Lys Pro Ala Ala His Leu Ile Gly Asp Pro Ser Lys Gln Asn Ser Leu Leu Trp Arg
CTT GCC CAC AGC ACC CTC AAA CCT GCT GCT CAC CTC ATT GGA GAC CCC AGC AAG CAG AAC TCA CTG CTC TGG AGA
     250                                                                300

                 50                                      60                                   70
Ala Asn Thr Asp Arg Ala Phe Leu Gln Asp Gly Phe Ser Leu Ser Asn Asn Ser Leu Leu Val Pro Thr Ser Gly
GCA AAC ACG GAC CGT GCC TTC CTC CAG GAT GGT TTC TCC TTG AGC AAC AAT TCT CTC CTG GTC CCC ACC AGT GGC
                                         350

                                  80                                      90
Ile Tyr Phe Val Tyr Ser Gln Val Val Phe Ser Gly Lys Ala Tyr Ser Pro Lys Ala Thr Ser Ser Pro Leu Tyr
ATC TAC TTC GTC TAC TCC CAG GTG GTC TTC TCT GGG AAA GCC TAC TCT CCC AAG GCC ACC TCC TCC CCA CTC TAC
     400                                                                450

                100                                     110                                   120
Leu Ala His Glu Val Gln Leu Phe Ser Ser Gln Tyr Pro Phe His Val Pro Leu Leu Ser Ser Gln Lys Met Val
CTG GCC CAT GAG GTC CAG CTC TTC TCC TCC CAG TAC CCC TTC CAT GTG CCT CTC CTC AGC TCC CAG AAG ATG GTG
                                         500
```

Fig. 2A.

```
                                        130                                                         140
Tyr Pro Gly Leu Gln Glu Pro Trp Leu His Ser Met Tyr His Gly Ala Ala Phe Gln Leu Thr Gln Gly Asp Gln
TAT CCA GGG CTG CAG GAA CCC TGG CTG CAC TCG ATG TAC CAC GGG GCT GCG TTC CAG CTC ACC CAG GGA GAC CAG
     550    PstI                                                        600

            150                                     160                                     170
Leu Ser Thr His Thr Asp Gly Ile Pro His Leu Val Leu Ser Pro Ser Thr Val Phe Phe Gly Ala Phe Ala Leu
CTA TCC ACC CAC ACA GAT GGC ATC CCC CAC CTA GTC CTC AGC CCT AGT ACT GTC TTC TTT GGA GCC TTC GCT CTG
                                        650

STOP
TAG  AACTTGGAAAAATCCAGAAAGAAAAAATAATTGATTTCAAGACCTTCTCCCCATTCTGCCTCCATTCTGACCATTTCAGGGGTCGTCACCACCTC
      700                                             750

TCCTTTGGCCATTCCAACAGCTCAAGTCTTCCCTGATCAAGTCACCGGAGCTTTCAAAGAAGGAATTCTAGGCATCCCAGGGGACCCACACTCCCTGAAC
      800                                             850    EcoRI

CATCCCTGATGTCTGTCTGGCTGAGGATTTCAAGCCTGCCTAGGAATTCCCAGCCCAAAGCTGTTGGTCTTGTCCACCAGCTAGGTGGGGCCTAGATCCA
      900                                             950

CACACAGAGGAAGAGCAGGCACATGGAGGAGCTTGGGGGATGACTAGAGGCAGGGAGGGGACTATTTATGAAGGCAAAAAAATTAAATTATTTATTTATG
     1000                                            1050

GAGGATGGAGAGAGGGAATAATAGAAGAACATCCAAGGAGAAACAGAGACAGGCCCAAGAGATGAAGAGTGAGAGGGCATGCGCACAAGGCTGACCAAGA
     1100                                            1150

GAGAAAGAAGTAGGCATGAGGGATCACAGGGCCCCAGAAGGCAGGGAAAGGCTCTGAAAGCCAGCTGCCGACCAGAGCCCCACACGGAGGCATCTGCACC
     1200                                            1250

CTCGATGAAGCCCAATAAACCTCTTTTCTCTGAAAAAAAAAAAAA   3'
     1300
```

Fig. 2A (Cont.)

ANTI-LYMPHOTOXIN

Reference is made to related copending U.S. Ser. No. 608,316 and U.S. Ser. No. 616,503, respectively, filed May 7, 1984 entitled "Human Lymphotoxin" and filed May 17, 1984 entitled "Recombinant Lymphotoxin ".

BACKGROUND

This application relates to lymphokines. In particular, it relates to lymphotoxin and derivatives thereof.

Lymphotoxin was first identified as a biological factor with anticellular activity on neoplastic cell lines. A substance identified as lymphotoxin and obtained from mitogen-stimulated lymphocytes has been demonstrated to have associated with it a spectrum of cytotoxic activities ranging from cytostasis of certain tumor cell lines to marked cytolysis of other transformed cells. On the other hand, lymphotoxin exhibits little or no anticellular activity on primary cell cultures and normal cell lines. This putative discriminating anticellular property of lymphotoxin led to in vivo studies which suggest that lymphotoxin may have a potent antitumor activity.

Purification and subsequent characterization of lymphotoxin proved difficult due to the small amount of activity secreted by primary lymphocyte cultures. The isolation and characteristics of lymphotoxin produced by the human lymphoblastoid cell line RPMI-1788 are described in Aggarwal et al., 1984, "J. Biol. Chem." 259(1): 686-691 and European patent application 100641 (published Feb. 15, 1984). This lymphotoxin is hereafter refered to as "lymphoblastoid" lymphotoxin.

Literature that should be studied in connection with this application includes J. Sawada, et al., 1976, "Jpn. J. Exp. Med." 46: 263-267; G. Granger, et al., 1978, "Cell. Immunol." 38: 388-402; J. Rundell, et al., 1981, "Immunopharmacology" 3:9-18; G. Granger, et al., 1982, "J. Lymphokine Res." 1: 45-49; N. Ruddle, et al., 1983, "Lymphokine Res." 2: 23-31; H. Ohnishi, et al., U.K. patent application No. 2,117,385; M. Mitsuhashi, et al., U.K. patent application No. 2,106,117; H. Enomoto, European patent application No. 87,087; B. Williamson, et al., 1983, "Proc. Natl. Acad. Sci. USA" 80: 5397-5401, and S. Wright et al., 1981, "J. Immunol." 126: 1516-1521.

It should be understood that lymphokine terminology is not uniform. At present, the names given to cell culture products are largely a function of the cells which elaborate the product and the performance of the products in biological assays. However, these products remain largely uncharacterized and their true identity will remain unknown in the absence of standard terminology based on clearly assayable distinguishing characteristics such as amino acid sequences or immune epitopes. Other names given to cytotoxic cell culture products include tumor necrosis factor, NK cell cytotoxic factor, hemorrhagic necrosis factor and macrophage cytotoxin or cytotoxic factor.

Lymphotoxin from RPMI-1788 has been isolated from culture supernatants as a putative aggregate having a molecular weight of about 60,000 Kd. This aggregate is resolved by purification into two molecular weight variants which differ in their amino terminal sequence. The larger variant, shown in FIG. 2*a* at amino acids 1-171 and having molecular weight of about 25,000 daltons, is distinguished by a leucyl amino terminal residue (hereafter "leucyl amino-terminal lymphotoxin"). The smaller 20,000 dalton variant also shown in FIG. 2*a* amino acids 24-171 contains a histidyl amino terminal residue (hereafter "histidyl amino-terminal lymphotoxin"). The literature contains reports of cytotoxic proteins found in supernatants from lymphocytes or lymphoblastoid cell lines which vary widely in molecular weight, from 12,000 to more than 200,000. It would be desirable to manufacture lymphotoxin having a substantially uniform molecular weight and uniform amino terminal amino acid sequence.

The lymphotoxin (or substances identified as lymphotoxin) obtained heretofore from lymphocyte culture are present in low concentrations, on the order of $0.05-2\times10^6$ units/l in supernatants of RPMI-1788 cells or peripheral blood lymphocytes. An economical method for producing uniform lymphotoxin is needed. Although the antitumor effects and apparent therapeutic value of lymphotoxin have been reported in the literature since at least 1976, lymphotoxin has not been studied in extensive clinical protocols or commercialized due to the small quantities and heterogenous nature of lymphotoxin produced in lymphocyte culture.

The characterization and purification of lymphotoxin would be facilitated by antibody raised against the lymphotoxin active or receptor binding site or an adjacent region which neutralizes the cytotoxic activity of lymphotoxin. The need for this antibody has been manifest for some time in the field of this application in view of the poorly characterized nature of cytotoxic lymph cell products and the need to purify and assay lymphotoxin, but as far as is presently known no publication of such an antibody is extant.

SUMMARY

We have isolated DNA which enables the accomplishment of the foregoing objectives. DNA which encodes lymphotoxin has been obtained which, when expressed, yields copious quantities of product upwards of 0.1 to $1\times10^{11}$ units/l of culture lysate.

The DNA sequence employed for the synthesis of lymphotoxin as provided herein is novel. cDNA obtained by reverse transcription of RPMI-1788 mRNA is distinguished from lymphotoxin chromosomal DNA by the absence of an intron in the codon for glycine between nucleotide positions 284 and 285 (FIG. 2*a*. In addition, or alternatively, the cDNA and chromosomal DNA which encodes lymphotoxin is obtained herein free of any flanking regions encoding other proteins of the organism from which the DNA originated.

This DNA or a fragment thereof is labelled and used in hybridization assays for genetic material encoding lymphotoxin or its homologues. The DNA, its fragments or derivatives, also are employed for the synthesis of lymphotoxin.

In processes for the synthesis of lymphotoxin, DNA which encodes lymphotoxin is ligated into a vector, the vector used to transform host cells, the host cells cultured and lymphotoxin recovered from the culture. This general process is used to construct lymphotoxin having the characteristics of lymphoblastoid lymphotoxin or to construct novel derivatives of lymphotoxin, depending upon vector construction and the host cell chosen for transformation. The lymphotoxin species which are capable of synthesis herein include leucyl amino-terminal lymphotoxin, histidyl amino-terminal lymphotoxin, pre lymphotoxin, and lymphotoxin derivatives including (a) fusion proteins wherein lymphotoxin and heterologous proteins or polypeptides are linked by a peptide bond at the amino and/or carboxyl terminal amino acids of lymphotoxin, (b) lymphotoxin fragments, especially fragments of pre lymphotoxin in which any amino acid between −34 and +23 is the amino-terminal amino acid of the fragment, (c) lymphotoxin mutants wherein one or more amino acid residues are substituted, inserted or deleted, (d) methionyl or modified methionyl (such as formyl methionyl or other blocked methionyl species) amino-terminal derivatives, and/or unglycosylated or variantly glycosylated species of all of the foregoing.

Ordinarily, if a mammalian cell is transformed with (a) a vector containing the entire structural gene of FIG. *2a*, or (b) the gene for leucyl amino-terminal lymphotoxin operably ligated to a eucaryotic secretory leader, and the cell cultured, then leucyl amino-terminal lymphotoxin is recovered from the culture.

Similarly, if DNA which encodes lymphotoxin is operably ligated in a vector to a procaryotic or yeast secretory leader which is recognized by the host cell to be transformed (usually the organism from which the leader sequence was obtained), the host transformed with the vector and cultured, then lymphotoxin, pre lymphotoxin and other nonmethionylated amino terminal lymphotoxin species ordinarily are recovered from the culture.

If DNA encoding lymphotoxin is operably ligated into a vector without a secretory leader sequence and then used to transform a host cell, the lymphotoxin species which are synthesized likely will be amino-terminal methionyl or modified methionyl such as formyl methionyl species.

Methods are provided to express lymphotoxin species not heretofore available. First, N-terminal methionyl or modified methionyl lymphotoxin is expressed by host cells transformed with DNA encoding lymphotoxin which is directly expressed, i.e., which is not operably linked to a secretory leader sequence. The same result is obtained upon transformation with a secretory leader sequence which is not recognized by the host, except that here the lymphotoxin is an N-terminal methionyl fusion protein.

Secondly, in vitro site-specific, predetermined or random mutagenesis can be employed to introduce deletions, substitutions and/or insertions into the DNA encoding lymphotoxin. The lymphotoxin derivatives obtained upon expression of this DNA exhibit modified characteristics.

The lymphotoxin species produced herein are purified from culture supernatants or lysates by immunoaffinity adsorption using insolubilized lymphotoxin-neutralizing antibody. This antibody, which is most efficiently produced in monoclonal cells culture, is raised in mice by immunization with alum-adsorbed lymphotoxin.

Finally, unglycosylated lymphotoxin is provided as a novel lymphotoxin species. This lymphotoxin is produced by expression of the lymphotoxin gene in procaryotes.

BRIEF DESCRIPTION OF THE DRAWINGS

FIG. *1a* shows the coding sequence, and corresponding putative expressed amino acid sequence, for a partial synthetic lymphotoxin gene.

FIG. *1b* demonstrates the construction of the synthetic gene.

FIG. *2a* shows the complete amino acid sequence for pre lymphotoxin, its coding DNA plus 5′ and 3′ flanking untranslated regions.

FIG. *2b* shows a method of constructing an expression vector for methionyl leucyl amino-terminal lymphotoxin and its amino terminal methionyl derivatives.

Figure 3:
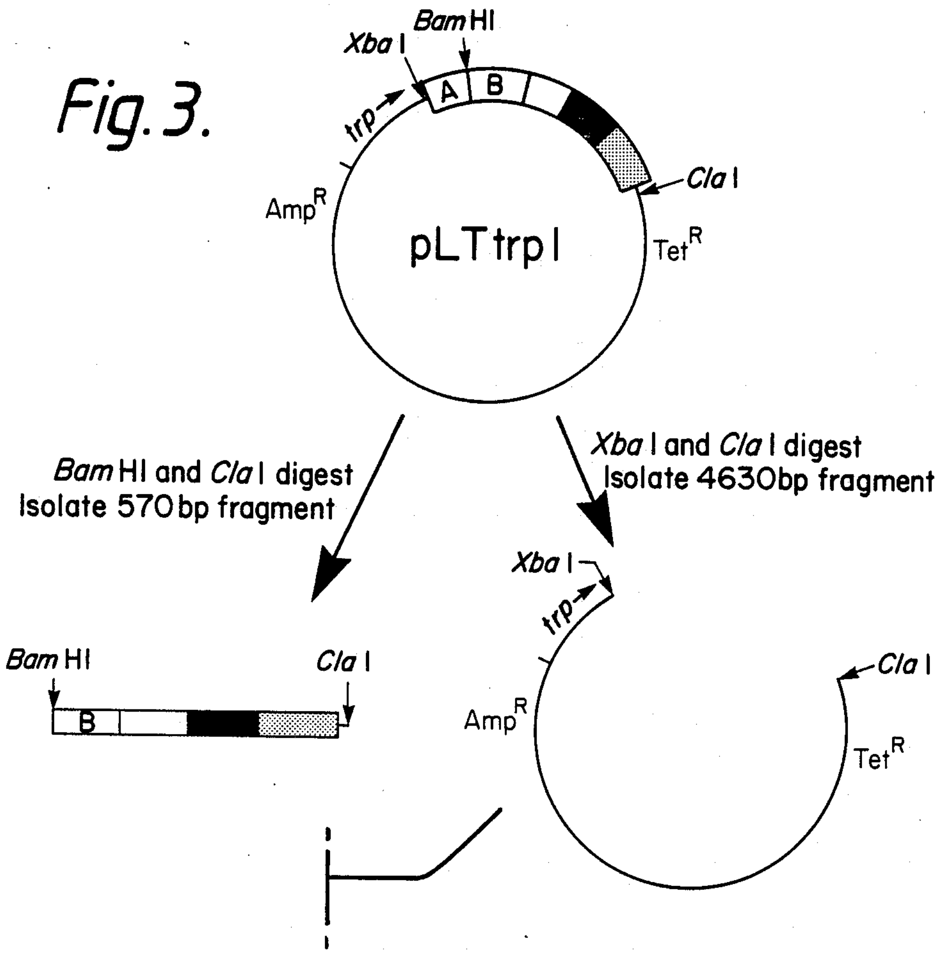
Figure 3:
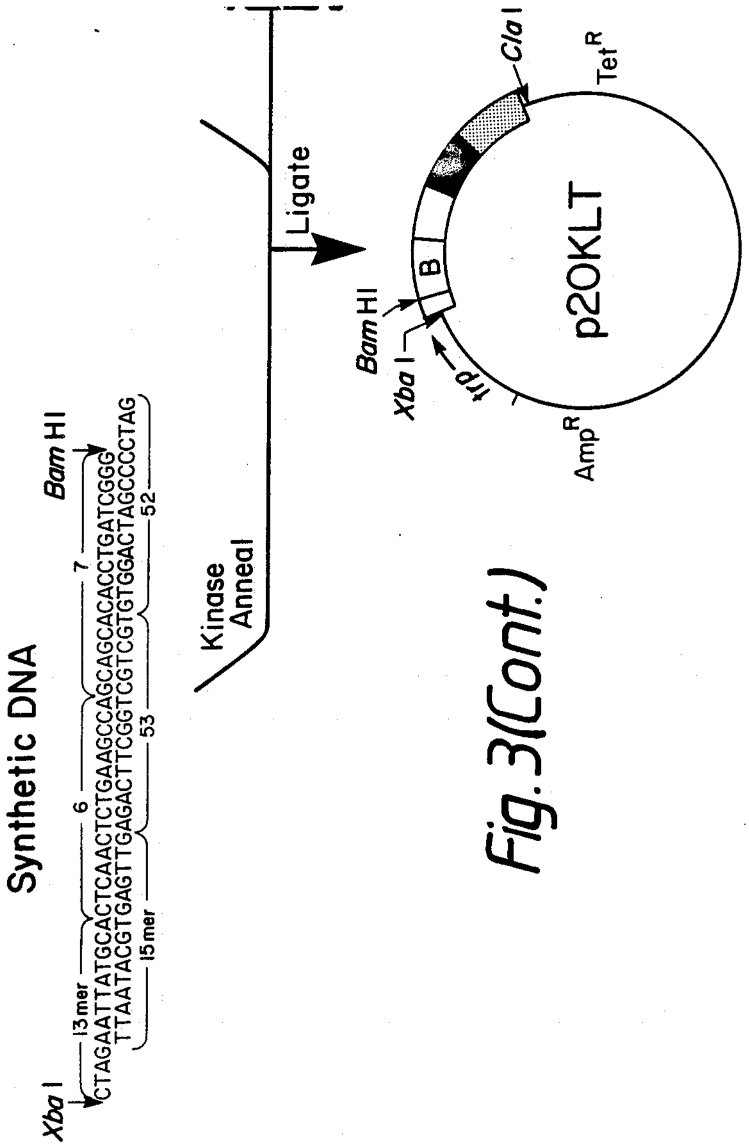

FIG. 3 shows a method of constructing an expression vector for methionyl histidyl amino-terminal lymphotoxin.

DETAILED DESCRIPTION

Lymphotoxin is defined for the purposes of this application as (1) a polypeptide capable either of cytotoxic activity towards tumor cells in vitro or tumor necrosis in vivo and (2) having a region demonstrating functional amino acid homology with the lymphotoxin amino acid sequence shown in FIG. *2a* or a fragment thereof.

Suitable assays for detecting the anticellular activities of lymphotoxin are described in B. Aggarwal, et al., 1984, "J. Biol. Chem." 259 (1), 686–691 and E. Carswell, et al., 1975, "Proc. Natl. Acad. Sci. USA" 72, 3666–3670. In general, anticellular or cytotoxic activity means a range of activities from cytostasis (antiproliferative activity) up to and including necrosis in vivo or cytolysis.

The degree of homology which brings a polypeptide within the scope of this definition will vary depending upon the lymphotoxin regions responsible for cytotoxic activity; domains which are critical for cytotoxic activity will exhibit a high degree of homology in order to fall within the definition, while sequences not involved in maintaining lymphotoxin conformation or in effecting receptor binding may show comparatively low homology. In addition, critical domains may exhibit cytolytic activity and yet remain homologous as defined herein if residues containing functionally similar side chains are substituted. Functionally similar refers to dominant characteristics of the side chains such as basic, neutral or acid, or the presence or absence of steric bulk. Generally a polypeptide defined as lymphotoxin will contain regions substantially homologous with the FIG. *2a* protein or fragments thereof over a region of about from 20 to 100 amino acid residues. Less homology is required in the amino terminal region than in the carboxy terminal region.

Lymphotoxin obtained by culture of lymphoblastoid cell lines has been determined to have the following characteristics: A molecular weight of 20,000 or 25,000, depending upon the degree of glycosylation and N-terminal heterogeneity., glycosylation, at Asn+62 (FIG. *2a*); a tendency to aggregate, particularly to organize into multimers; an isolectric point of about 5.8; pH lability (a loss of >50 percent of cytolytic activity when stored for 24 hours in ammonium bicarbonate buffer at 10 $\mu$g/ml concentration with pH levels less than about 5 or greater than about 10); and substantial losses in activity upon incubation in aqueous solution for 5 min. at 80° C. It is important to observe that these characteristics describe the native or wild type lymphoblastoid human lymphotoxin obtained from lymphoblastoid cell cultures. While lymphotoxin as defined herein includes such lymphotoxin, other related cytotoxic polypeptides many fall within the scope of the definition. For example, the glycosylation of animal lymphotoxin may be sufficiently distinct to bring it outside of the molecular weights established for human lymphoblastoid lymphotoxin. In addition, post-translational processing of animal pre lymphotoxin in cell lines derived from nonprimate mammals may produce considerably different microheterogeneity in the amino terminal region than has been observed for human lymphoblastoid lymphotoxin. Similarly, the mutagensis procedures provided herein, for example, will enable one to vary the amino acid sequence and N-terminus of lymphotoxin.

The translated amino acid sequence for human lymphotoxin is described in FIG. 2*a*. Note that this sequence includes a 34 residue presequence which is believed to be removed during normal processing of the translated transcript in human cells (herein, together with its mutants, "pre lymphotoxin"), resulting in the leucyl amino terminal species. The histidyl amino-terminal species is generated from the leucyl amino-terminal species. All three species, i.e. pre lymphotoxin, leucyl amino-terminal lymphotoxin and histidyl amino-terminal lymphotoxin, as well as their methionyl, modified methionyl, and unglycosylated forms, are included within the scope of lymphotoxin. Note that when lymphotoxin is unglycosylated the leucyl and histidyl amino-terminal species will have lower molecular weights than described above for these species from lymphoblastoid cells.

Note that the language "capable" of cytolytic or in vivo tumor necrosis means that lymphotoxin includes polypeptides which can be converted, as by enzymatic hydrolysis, from an inactive state analogous to a zymogen to a polypeptide fragment which exhibits the desired biological activity. The fragment that is so generated may be pre lymphotoxin, leucyl amino-terminal lymphotoxin, histidyl amino-terminal lymphotoxin, derivatives thereof, or any other polypeptide falling within the foregoing definition of lymphotoxin.

While lymphotoxin ordinarily is meant to mean human lymphotoxin, lymphotoxin from sources such as murine, porcine, equine or bovine is included within the definition of lymphotoxin so long as it otherwise meets the standards described above for homologous regions and biological activity.

lymphotoxin also includes multimeric forms. Lymphotoxin spontaneously aggregates into multimers, usually dimers or higher multimers. Multimers are cytotoxic and accordingly are suitable for use in in vivo therapy. While it is desirable to express and recover lymphotoxin in a homogeneous form, permitting lymphotoxin to form a mixture of different multimers is not believed to be disadvantageous.

Derivatives of lymphotoxin include targeted, i.e. site specific, mutations of the FIG. 2*a* molecule or its fragments. The objective of mutagenesis is to construct DNA that encodes lymphotoxin as defined above, i.e., which lymphotoxin exhibits cytotoxic activity towards tumor cells in vitro or tumor necrosis in vivo and retains residual FIG. 2*a* lymphotoxin homology. For example, the lysine +89 codon is mutated in order to express a histidine residue in place of the lysine residue. The histidine +89 lymphotoxin mutant retains cytotoxic activity, yet it is no longer hydrolyzed by trypsin (which cleaves proteins at an arg-X or lys-X bond). Protease resistance is expected to confer greater biological half life on the mutant than is the case for lymphotoxin having the sequence of FIG. 2*a* (or a fragment thereof). Other lymphotoxin lysine or arginine residues may be mutated to histidine, for example lysine +28, lysine +19 or arginine +15.

While the mutation site is predetermined, it is unnecessary that the mutation per se be predetermined. In order to optimize the performance of the mutant histidine +89 lymphotoxin, random mutagenesis may be conducted at the codon for lysine +89 and the expressed lymphotoxin mutants screened for the optimal combination of cytotoxic activity and protease resistance.

Lymphotoxin also may contain insertions, usually on the order of about from 1 to 10 amino acid residues, or deletions of about from 1 to 30 residues. Substitutions, deletions, insertions or any subcombination may be combined to arrive at a final construct. Preferably, however, only substitution mutagensis is conducted.

Not all mutations in the DNA which encodes the lymphotoxin will be expressed in the final secreted product. For example, a major class of DNA substitution mutations are those DNAs in which a different secretory leader has been substituted for the FIG. 2*a* secretory leader, either by deletions within the 34 residue leader or by substitutions, which exchange of most or all of the native leader for a leader more likely to be recognized by the intended host. For example, in constructing a procaryotic expression vector the FIG. 2*a* secretory leader is deleted in favor of the bacterial alkaline phosphatase or heat stable enterotoxin II leaders, and for yeast the FIG. 2*a* leader is substituted in favor of the yeast invertase, alpha factor or acid phosphatase leaders. This is not to imply, however, that the human secretory leader is not recognized by hosts other than human cell lines. When the secretory leader is "recognized" by the host, the fusion protein consisting of lymphotoxin and the leader ordinarily is cleaved at the leader-lymphotoxin peptide bond in the same event that leads to secretion of the lymphotoxin. Thus, even though a mutant DNA is used to transform the host the resulting product lymphotoxin may be either a mutant or any of the lymphoblastoid derivatives such as leucyl amino-terminal lymphotoxin.

A vector is a replicable DNA construct. Vectors are used herein to amplify. DNA or to express DNA which encodes lymphotoxin. An expression vector is a DNA construct in which a DNA sequence encoding lymphotoxin is operably linked to a suitable control sequence capable of effecting the expression of lymphotoxin in a suitable host. Such control sequences include a transcriptional promoter, an optional operator sequence to control transcription, a sequence encoding suitable mRNA ribosomal binding sites, and sequences which control termination of transcription and translation.

The vector may be a plasmid, a virus (including phage), or an integratable DNA fragment (i.e., integratable into the host genome by recombination). Once transformed into a suitable host, the vector replicates and functions independently of the host genome, or may, in some instances, integrate into the genome itself. In the present specification, "plasmid" and "vector" are sometimes used interchangeably as the plasmid is the most commonly used form of vector at present. However, all other forms of vectors which serve an equivalent function and which are, or become, known in the art are suitable for use herein.

Suitable vectors ordinarily are selected on the basis of the intended expression host. For example, a Bacillus vector will contain a Bacillus origin of replication, a promoter which will function in Bacilli and a selection gene, for example a gene encoding proteins conferring antibiotic resistance or supplying an auxotrophic requirement. Similar constructs will be manufactured for other hosts. In the case of *E. coli*, the vector preferably comprises the trp promoter (D. Goeddel et al., 1980, "Nature" 287:441–416) operably linked to the lymphotoxin sequence. Other promoters such as those for the beta galactosidase or histidine operons are satisfactory.

The yeast vectors may contain promoters for metallothionein and glycolytic enzymes operably linked to the lymphotoxin coding sequence. Suitable yeast vectors and promoters also include those described in R. Hitzeman et al., European patent application 73,657 and references cited therein.

Vectors for use with higher eucaryotic host cells include viral promoters, e.g., SV40 early and late promoters, structural gene promoters, e.g., metallothionein or the lymphotoxin promoter, and terminator regions from the hepatitis B virus surface antigen or the lymphotoxin wild type terminator. Preferably, these vectors will include the lymphotoxin gene operably linked to and under the control of the SV40 early promoter and the hepatitis B surface antigen terminator region.

Transformed host cells are cells which have been transformed or transfected with lymphotoxin vectors constructed using recombinant DNA techniques. Transformed host cells ordinarily express lymphotoxin. The expressed lymphotoxin may be deposited intracellularly or secreted into the periplasmic space or the culture supernatant.

DNA regions are operably linked when they are functionally related to each other. For example, DNA for a presequence or secretory leader is operably linked to DNA for a polypeptide if it is expressed as a preprotein participating in the secretion of the polypeptide; a promoter is operably linked to a coding sequence if it controls the transcription of the sequence; or a ribosome binding site is operably linked to a coding sequence if it is positioned so as to permit translation.

Suitable host cells are procaryotes, yeast or higher eucaryotic cells. Procaryotes include gram negative or gram positive organisms, for example *E. coli* or Bacillus species. Higher eucaryotic cells include established cell lines of mammalian origin, e.g. CHO (Chinese hamster ovary), COS (monkey) or HeLa (human). Other suitable hosts will be apparent to those skilled in the art.

Lymphotoxin is recovered from recombinant culture in nonsecreting cells by lysing the cells and removing particulate matter by centrifugation or the like. Lymphotoxin secreting cells are separated from culture supernatant by centrifugation. The contaminated lymphotoxin solution is then purified by the methods referred to above or by immunoaffinity as described in Example 4 below. The lymphotoxin is purified to levels suitable for pharmacological use and placed into conventional dosage forms, e.g. vials or syringes. Lymphotoxin optimally is lyophilized for long term storage, or it may be placed in aqueous solution with stabilizers and excipients, for example isotonic saline, and administered to patients as disclosed by B. Aggarwal et al., European patent application 100641.

A method is provided herein for obtaining lymphotoxinneutralizing antibody. Neutralizing antibody is defined as antibody that is capable of immunologically binding lymphotoxin as defined herein in such a way as to substantially reduce its activity in cytostatic or cytolytic lymphotoxin activity assays such as the murine L929 assay described below. The fact that the antibody is capable of neutralizing lymphotoxin activity does not mean that the antibody must bind directly to the lymphotoxin active or receptor binding site. The antibody may still substantially neutralize lymphotoxin activity if it sterically binds to a region which adjacent to the critical site, i.e., adjacent in the sense of conformationally adjacent and not necessarily adjacent from the point of view of amino acid sequence.

It proved difficult to immunize mice in a fashion such that lymphotoxin neutralizing antibody is generated or raised in the animals. Neither immunization with lymphoblastoid lymphotoxin nor glutaraldehyde cross-linked lymphotoxin resulted in any detectable neutralizing antibody in the serum of immunized mice, even though the mice did raise non-neutralizing anti-lymphotoxin antibody detectable by enzyme immunoassay. However, immunization with a lymphotoxin alum (aluminum hydroxide or alumina, $Al_2O_3$ $3H_2O$ adsorption complex will raise neutralizing antibody even in animals which had failed to generate the activity prior to immunization with the alum complex. Preparation of alum and its use in the production of antiserum are disclosed in C. Williams, et al., eds., 1967, *Methods in Immunology and Immunochemistry* I, pp 197–229.

Fusions of spleen cells from animals producing neutralizing antibody with murine myeloma cells are made in order to generate hybridomas so that, on the average, about 50 to 100 clones will have to be screened to identify one which synthesizes neutralizing antibody. The process for screening the clones for the desired activity is routine and well within the skill of the ordinary artisan, and can be reproduced with minimal experimental effort.

The serum plasma or IgG fractions from the immunized animal, as well as immunoglobulins secreted by hybridoma generated from the spleen or lymph cell of immunized animals, are all satisfactory for use herein. In a preferred embodiment the neutralizing antibody is obtained essentially free of other anti-lymphotoxin antibody, whether by hybridoma culture or by immunoaffinity purification on immobilized lymphotoxin of polyclonal sera from mice or other animals such as rabbits. Hybridoma culture is preferred. For this reason, it is preferred to immunize mice to locate animals which produce neutralizing antibodies.

The neutralizing antibody is immobilized by adsorption to surfaces, e.g., thermoplastics such as polystyrene, or covalently bound to matrices such as cyanogen bromide-activated Sepharose. It then is used in immunoassays or in immunoaffinity purification. Since the antibody is a neutralizing antibody it is most likely to only purify or detect biologically active lymphotoxin or fragments thereof. The antibody is particularly useful in immunoradiometric ("sandwich")immunoassays in concert with a non-neutralizing anti-lymphotoxin monoclonal antibody or a polyclonal antiserum which contains non-neutralizing anti-lymphotoxin. The immunoassay is conducted using either the neutralizing or non-neutralizing antibody as the labelled component, which labelling is effective with a detectable substance such as a fluorescent, chemiluminescent or radioisotopic label in accord with methods known in the art. For competitive-type lymphotoxin immunoassays, lymphotoxin is labelled in the same fashion. Chloramine-T radioiodination is preferred for both lymphotoxin and lymphotoxin antibody tracer preparation.

Glossary of Experimental Manipulations

In order to simplify the Examples certain frequently occurring methods will be referenced by shorthand phrases.

Plasmids are designated by a low case p preceded and/or followed by capital letters and/or numbers. The starting plasmids herein are commercially available, are publically available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, Molecular Cloning pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9:6103–6114, and D. Goeddel et al., 1980, "Nucleic Acids Res." 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98:503–517, and hybridization as described by. T. Maniatis et al., 1978, "Cell" 15:687–701.

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53:154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by the method incorporated by reference into Example 1, and then purified on polyacrylamide gels.

All literature citations are expressly incorporated by reference.

EXAMPLE 1

Purification and Sequencing of Lymphotoxin

The human lymphoblastoid cell line RPMI-1788 (ATCC No. CCL-156) was grown in 15 L spinner flasks to a cell density of $4\times10^5$ cells per ml using a serum free culture medium (RPMI-1640). Lymphotoxin was induced 10–20 fold (to 500–1000 lymphotoxin units/ml, determined as described below) over basal levels by the inclusion of 20 ng/ml of phorbol myristate acetate in the serum free RPMI-1640 medium. After 65 h of culture, the cells were harvested by filtration, and the lymphotoxin activity in the filtrate was absorbed to controlled pore glass beads (Electronucleonics) in a column (5 cm×20 cm), equilibrated with 5 mM phosphate buffer (pH 7.4) and eluted with 50 percent ethylene glycol in 5 mM phosphate buffer (pH 7.4). 0.1 mM phenylmethyl sulfonyl fluoride (PMSF), a protease inhibitor, and 1 mM sodium azide, for inhibition of microbial growth, were included in all buffers throughout the purification. The eluate from glass beads contained 84,000 units of lymphotoxin/mg protein. This was followed by DEAE cellulose chromatography., Lentil Lectin Sepharose chromatography, and preparative native PAGE as described in B. Aggarwal, et al., 1984, "J. Biol. Chem." 259 (1): 686–691. Homogeneity of the protein responsible for cytotoxic activity was determined by SDS-PAGE, reverse-phase HPLC on a Lichrosorb RP-18 column and by amino terminal sequencing.

This lymphotoxin preparation contained greater than 95 percent by weight of the leucyl amino-terminal lymphotoxin having an approximate molecular weight of 25,000 on SDS-PAGE. The theoretical molecular weight of the protein component of the N-terminal leucyl species is 18,664 daltons; the remaining approximately 6,500 daltons was attributed to a glycosyl side chain at Asn+62, and perhaps other 0-linked sugar residues. The tissue culture supernatant contained putative multimers of this species (60,000 Da by TSK-HPLC or 64,000 Da by Sephadex G-100 chromatography).

The remaining 5 percent of the lymphotoxin mixture was the N-terminal histidyl species having a molecular weight of about 20,000. Both species exhibit substantially the same cytolytic activity, at least within the limits of the variation inherent in the murine fibroblast cell lysis assay described below.

Tryptic digestion of the intact lymphotoxin molecules yielded only a few fragments. Histidyl amino-terminal lymphotoxin was digested into two fragments between amino acid positions 89 and 90, while the leucyl amino-terminal tryptic and digestion yielded four fragments cleaved between positions 15 and 16, 19 and 20, and 89 and 90.

Micro-sequencing by the Edman degradation technique yielded sequence information on the intact molecule and also on the fragments produced by tryptic cleavage.

Further sequence information was provided by fragments of lymphotoxin produced by carboxypeptidase P and chymotrypsin digestion, acetic acid digestion and cyanogen bromide cleavage. Nearly the entire sequence of the human lymphotoxin was determined by this method. 156 contiguous residues were determined from the amino terminus. It was clear from this sequencing information that the difference between the two lymphotoxin species was the presence of 23 amino-terminal residues in the leucyl amino-terminal species which were not found in the histidyl amino-terminal species. The carboxyl terminal sequence proved to be difficult to determine because of certain peptide bonds present in this region and the hydrophobic nature of the residues.

A synthetic gene was designed which would code for the protein sequence to the extent determined by micro-sequencing. The gene design incorporated a general *E. coli* codon bias, that is, rarely used *E. coli* codons were not used in the sequence. Human preference codons were substituted where no *E. coli* codon bias was apparent. This bias was chosen to aid in expression in *E. coli,* and also so that the synthetic gene would be useful as a probe to identify the natural DNA sequence from human cDNA or genomic libraries. The unique restriction sites XbaI, BamHI, HindIII, and BglII were designed into the sequence to aid in the construction of the fragments and to allow for future manipulation of the gene.

Figure 1A:
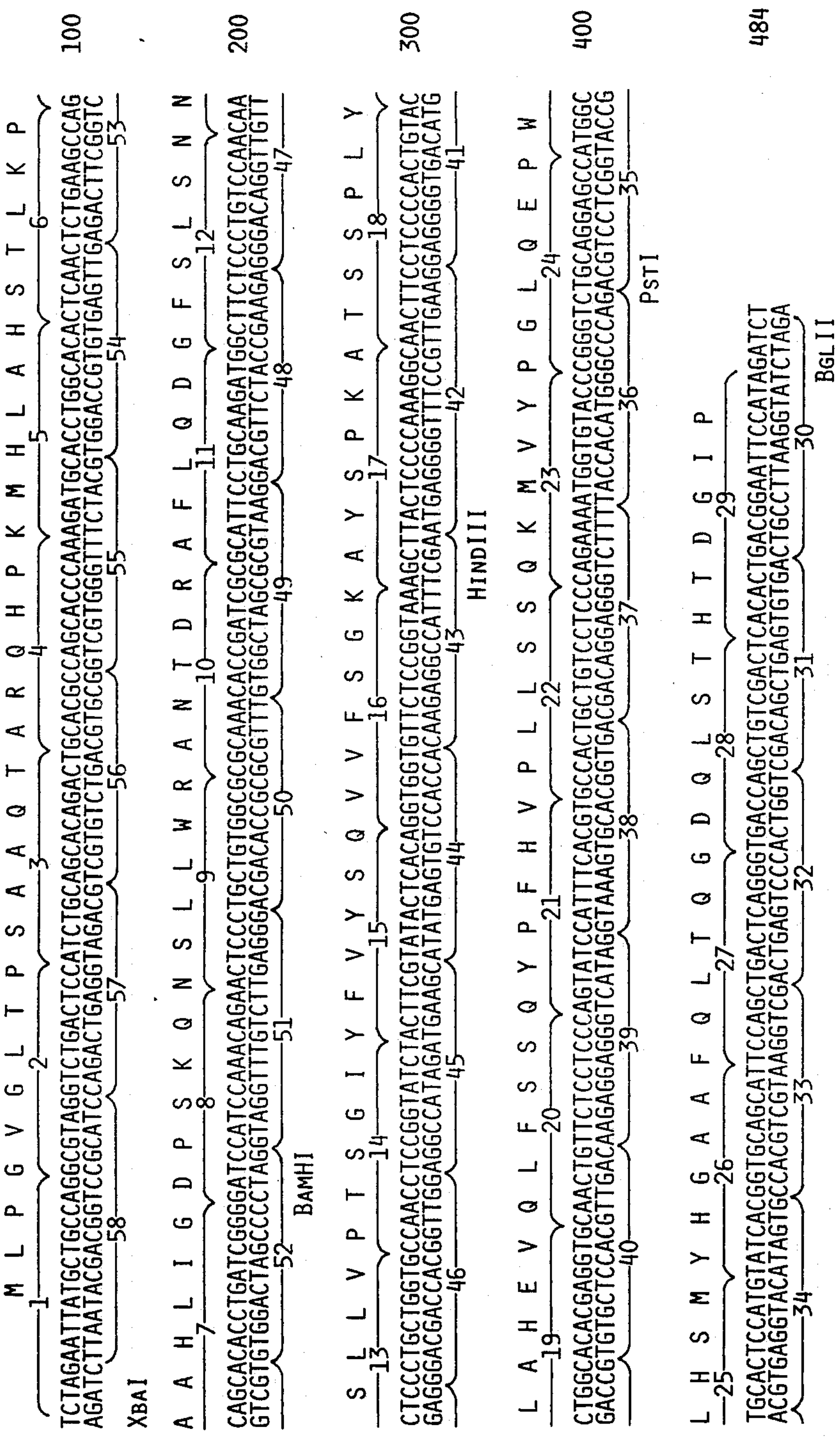
Figure 1B:
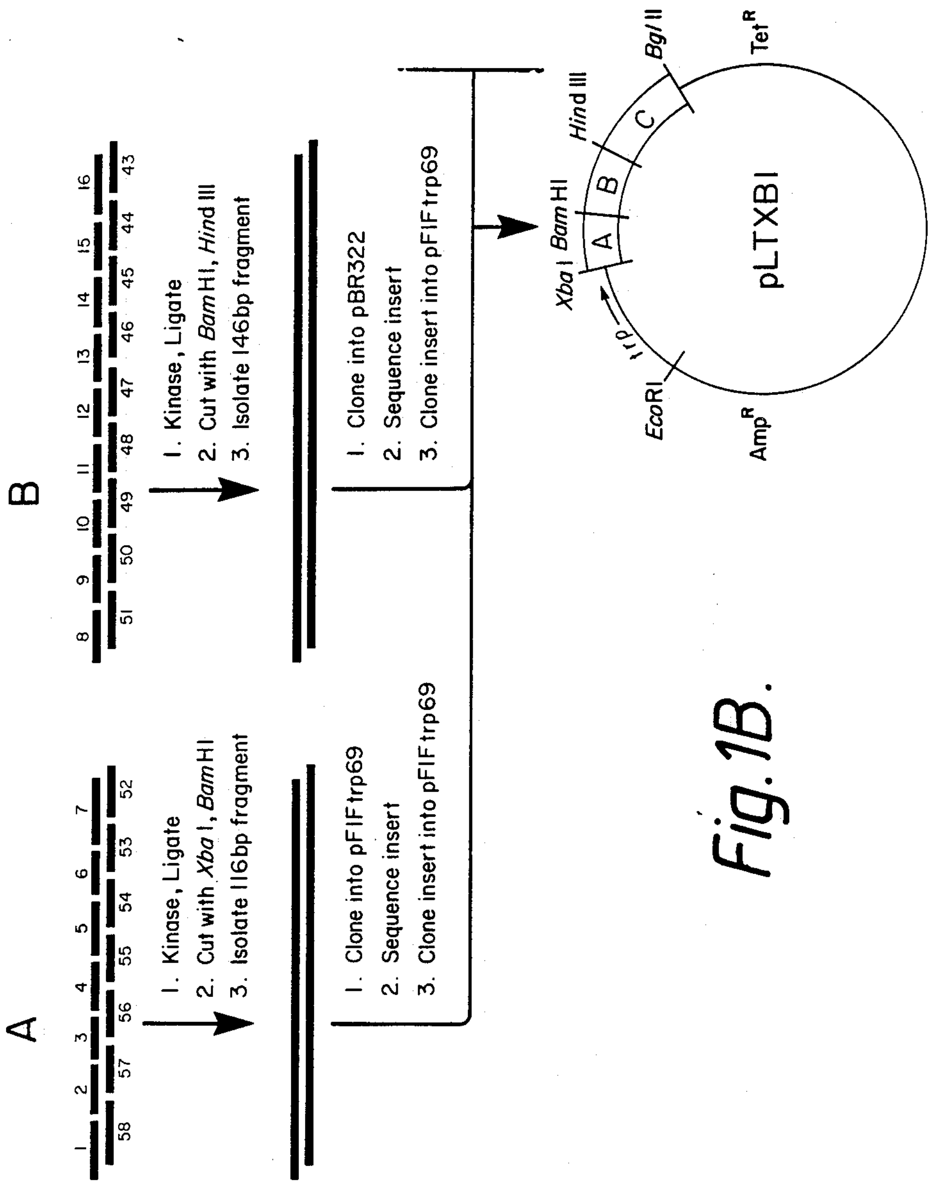
Figure 1B:
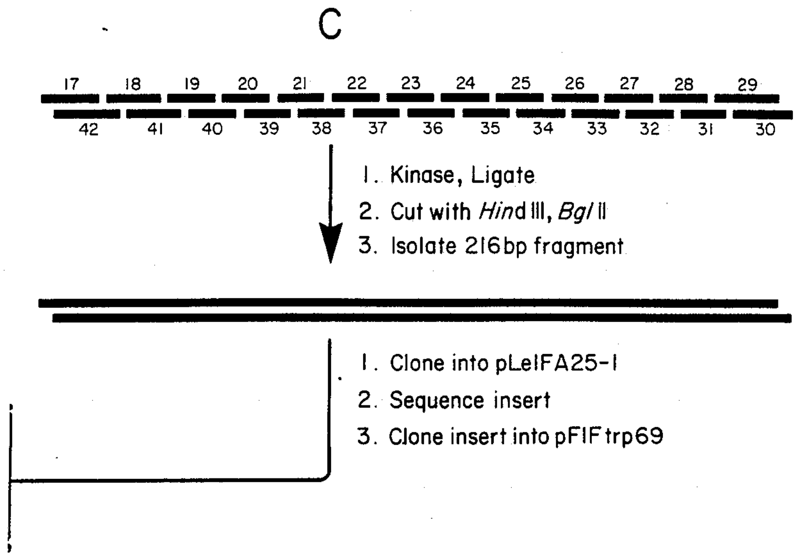

The 58 original oligomers designed for the synthetic lymphotoxin gene were synthesized by the solid phase phosphite method of M. Matteucci et al., 1981, "J. Amer. Chem. Soc." 103: 3185–3190 and S. Beaucage et al., 1981, "Tet. Letters" 22: 1859–1862. The size of these oligomers ranged from 16 bases to 20 bases and is shown in FIG. 1*a.* Overlaps between oligomers were 6 bases in length and designed to be unique. The entire gene was assembled as shown in FIG. 1*b.*

The gene was constructed in three separate pieces. The first, Segment A, was 117 base pairs in length and represented the 5' coding region for the amino terminal end of the leucyl amino-terminal species. Segment B represented the DNA encoding the middle of the lymphotoxin molecule and was 145 base pairs in length. Segment C, at 217 base pairs in length, was believed to encode all but 16 amino acid residues at the lymphotoxin carboxy terminus. The oligomers required to synthesize each of the segments were purified by electrophoresis and then pooled. The relatively small size of each oligomer (that is, 16 to 20 bases) was chosen to reduce errors in synthesis.

Each group of oligomers was phosphorylated in a reaction containing 20 mM Tris-HCl (pH 7.5), 10 mM $MgCl_2$, 20 mM dithiothreitol, 0.5 mM ATP, and 15 units of T4 polynucleotide kinase in a volume of 50 $\mu$l; approximately 50 pmol of each oligomer was contained in the reaction. After 30 minutes at 37° C., the reaction was heated to 65° C. to destroy kinase activity, and then allowed to slowly cool to 20° C. over the period of one hour. The phosphorylated oligomers were then ligated by the addition of 10 units of T4 DNA ligase and the reaction was allowed to proceed for 2 hours at 20° C. The DNA ligase was heat inactivated and then the ligated oligomers were digested for 3 hours at 37° C. with restriction endonucleases which recognized the designed terminal sites (e.g., XbaI and BamHI for segment A). Fragments for each segment were isolated by electrophoresis on a 7 percent polyacrylamide gel. Fragments of the correct mobility were identified for each segment by ethidium bromide staining and electroeluted from the gel. pFIFtrp69 (D. Goeddel et al., 1980, "Nature" 287: 411–416 or Crea et al., European patent application 0048970) was digested with XbaI and BamHI and the large vector fragment isolated by 6 percent polyacrylamide gel electrophoresis. About 50 ng of segment A was ligated to the pFIFtrp69 fragment. Similarly, segment B was ligated into BamHI and HindIII digested pBR322, and segment C was ligated into HindIII and BglII digested pLeIFA-125-1 (D. Goeddel et al., 1980, "Nuc. Acids Res." 8: 4057–4073). The ligation reaction mixtures were transformed into *E. coli* ATCC 31446 and the resulting recombinant plasmids were characterized by restriction endonuclease analysis and DNA sequencing by the Maxam and Gilbert chemical degradation method. Five of six segment A clones contained the designed sequence. Four segment B and four segment C plasmids were isolated, and all of these inserts had the correct sequences. Each segment was isolated by digestion with restriction endonucleases which recognized the terminal sites and then ligated into the plasmid vector pFIFtrp69 digested with XbaI and BglII. The resulting recombinant plasmid, pLTXB1, was characterized by sequencing the inserted XbaI-BglII fragment, which contained the sequence presented in FIG. 1*a.*

To determine if the synthetic gene would indeed produce biologically active lymphotoxin, the *E. coli* pLTXB1 transformants were grown in minimal media under conditions to de-repress the trp promoter and allow expression of the synthetic lymphotoxin gene. Cultures were grown to an optical density of 1.0 at 550 nanometers and harvested by centrifugation. The cell pellet was suspended in one-tenth volume, and then lysed by sonication.

Lymphotoxin activity was determined by the modified cell-lytic assay of B. Spofford, 1974, "J. Immunol." 112: 2111. Briefly, mouse L-929 fibroblast cells were grown in microtiter plates in the presence of actinomycin D. After 12–18 hours, 0.125 ml of serially diluted sample to be assayed for lymphotoxin is added to each well. After 18 hours, the plates were washed and the lysis of the cells induced by lymphotoxin was detected as adhering to the plates by staining the plates with a 1 percent solution of crystal violet in methanol:water (1:4 v/v). The intensity of stain was observed both visually as well as spectrophotometrically at absorbance of 450 nm and 570 nm transmission using a Dynatech spectrophotometer. The cells plated in a microtiter well with culture medium alone were set at 0 percent lysis whereas those with 3M guanidine hydrochloride solution provided an end point for 100 percent lysis. One unit of lymphotoxin is defined as the amount required for 50 percent cell lysis out of 12,000 cells plated in each well. Note that other assays of cytotoxic activity also may be used. For example see B. Aggarwal et al., in "Thymic Hormones and Lymphokines", 1983, ed. A.

Goldstein, Spring Symposium on Health Sciences, George Washington Univ. Medical Center (the A549 cell line referred to in this material is available from the ATCC as CCL185). Culture lysates showed undetectable cytolytic activity in the murine cell assay described above. Control lysates from gamma interferon expressing cultures did contain gamma interferon activity. This result suggested that the synthetic gene did not encode an active lymphotoxin. There were several possible explanations for this. For example, (1) the *E. coli* degraded the lymphotoxin, (2) the lymphotoxin gene was not transcribed in *E. coli,* (3) the lymphotoxin message was not translated in *E. coli,* (4) the protein did not have the proper sequence due to a protein sequencing error, or (5) the 16 residue carboxy terminal sequence or a portion thereof was actually necessary for activity or for proper configuration of the lymphotoxin molecule.

EXAMPLE 2

Procedure for Obtaining cDNA for Lymphotoxin

RNA was isolated from a culture of a non-adherent cell fraction of human peripheral blood lymphocytes 48 hours after induction with phorbol myristate acetate (10 ng/ml), staphylococcal enterotoxin B (1 μg/ml) and thymosin α-1 (S. Berger et al., 1979, "Biochemistry" 18: 5143–5149). This culture was producing 400 units of lymphotoxin activity/ml of supernatant. The mRNA was concentrated by adsorption to immobilized oligo dT, eluted and cDNA prepared by reverse transcription (P. Gray et al., 1982, "Nature" 295: 503–508). Reverse transcriptase was used to make a cDNA copy of the messenger RNA by standard methods, and a second strand was prepared (also by standard methods) by Klenow treatment. The cDNA was treated with S-1 nuclease to remove the hairpin loop, synthetic DNA was ligated to the cDNA to create EcoRI cohesive termini. λgt10, a publicly available phage (or its substantial equivalent, λgt11, which is available from the ATCC), was digested with EcoRI and the linear fragment recovered (M. Wickens et al., 1978, "j. Biol. Chem." 253: 2483–2495). The linkered reverse transcript and the λgt10 digest were ligated and the ligation mixture used to transfect *E. coli* C-600 or other known host susceptible to λ phage infection. Approximately 10,000 recombinant phage were plated on a 15 cm plate and screened by a low-stringency plaque hybridization method (T. Maniatis et al., 1978, "Cell" 15: 687–701 and P. Gray et al., "PNAS" 80: 5842–5846) using a $^{32}$P-labelled probe was prepared from Segment A of FIG. 1*a* by the method of J. Taylor et al., 1976, "Biochem. Biophys. Acta" 442: 324–330 in which calf thymus DNA primers were used (PL Biochemicals). Duplicate nitrocellulose filters were hybridized by the low stringency method with $5\times10^7$ cpm of the probe in 20 percent formamide. The filters were washed twice in 0.3 M sodium chloride, 0.03 M sodium citrate, and 0.1 percent sodium dodecyl sulfonate (SDS) at 37° C.

Two phage hybridized with the probe and were plaque purified. The purified phage hybridized with both the Segment A probe and a probe prepared from Segment B. The cDNA inserts of the two hybridizing phage, λLT1 and λLT2, were subcloned into M13mp8 and sequenced by the dideoxy chain termination method (A. Smith, 1980, "Methods in Enzymology" 65: 560–580). The insert in λLT2 was only about 600 bp and did not contain the entire 3′ coding region for lymphotoxin. The insert in λLT1 contained the entire coding region for leucyl amino-terminal lymphotoxin plus a 650 bp 3′ untranslated region (containing a consensus polyadenylation signal) and codons for 18 amino acids amino terminal to the leucyl terminus. Since this did not constitute the entire lymphotoxin coding region an additional $^{32}$P-labelled probe was prepared from the insert of λLT1 and used to screen an additional 25,000 recombinant λgt10 phage at high stringency (see T. Huynh et al., 1984, in Practical Approaches in Biochemistry IRL Press, Oxford). Twelve additional hybridizing phage were isolated and the sequence of the longest insert, from λLT11, is presented in FIG. 2*a.* The longest open reading frame was translated starting at the first observed ATG. Numbers above each line refer to amino acid position and numbers below each line refer to nucleotide position. The leucyl residue labelled "1" represents the first residue sequenced of leucyl amino-terminal lymphotoxin (FIG. 1*a*) and is presumably the first amino terminal residue of the mature species of lymphotoxin. The first 34 residues represent a signal sequence. Residues 156–171 had not been determinable by protein sequencing of lymphotoxin, but instead were imputed from the nucleotide sequence.

EXAMPLE 3

Figure 2B:
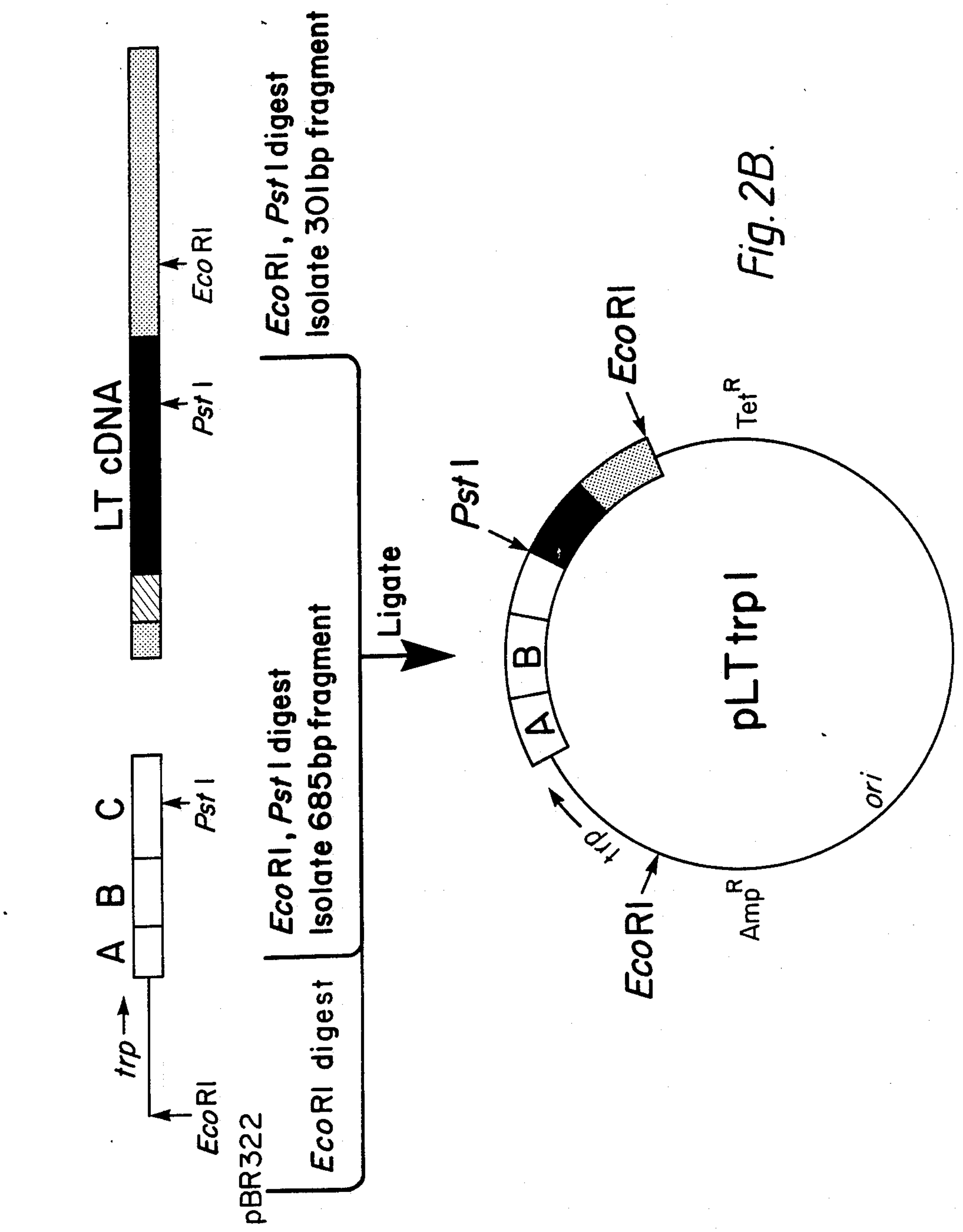

Construction of a Hybrid Synthetic Gene/Natural cCNA Expression Vector for Leucyl Amino-Terminal Lymphotoxin This construction is shown in FIG. 2*b.* pLTXB1 (containing the inactive synthetic gene) was partially digested with EcoRI and PstI, and a 685 bp fragment containing DNA encoding 125 N-terminal residues of lymphotoxin was recovered. A partial PstI digest was performed because of the presence of an additional PstI site at residue 10 (FIG. 1*a*). A 301 bp fragment containing DNA encoding the C-terminal 51 amino acids of lymphotoxin was isolated by digesting the subcloned cDNA of λLT1 with EcoRI and PstI (these sites are shown above in FIG. 2*a* at nucleotide positions 554 and 855). These fragments were isolated by electrophoresis on 5 percent polyacrylamide and electroelution. The fragments were ligated into pBR322 which had been digested with EcoRI and dephosphorylated with bacterial alkaline phosphatase to reduce background transformants. The resulting expression plasmid, pLTtrp1, was characterized as to proper orientation and sequence by restriction endonuclease digestion and DNA sequencing. Leucyl amino-terminal lymphotoxin was expressed by transforming *E. coli* 31446 with pLTtrp1 and culturing the transformants in medium containing tetracycline at 37° C. for 4–6 hours until an OD. of 1.0 was reached. The leucyl amino terminus of this species was found substituted with a blocked methionyl residue. It is believed that the product of this synthesis is the formyl methionyl rather than methionyl species.

EXAMPLE 4

Immunoaffinity Purification of Lymphotoxin

A murine monoclonal cell line secreting anti-lymphotoxin (Example 8) was grown in mice and purified from ascites fluid by ion exchange chromatography. The anion exchange eluate was coupled to cyanogen bromide activated Sepharose at a concentration of 2 mg/ml resin. A 20 ml column was equilibrated consecutively with TBS (containing 0.05 M Tris-HCl, pH 7.5, 0.15 M sodium chloride, and 2 mM EDTA); then with elution buffer (containing 0.1 M acetic acid, pH 4.5, 150 mM sodium chloride); and finally with TBS. A 40 percent saturated ammonium sulfate precipitate of pLTtrp1-transformed *E. coli* sonicated lysate was suspended in 0.1 M Tris-HCl, pH 7.4, and 5 mM EDTA and loaded onto the column at a rate of one column volume per hour. Following extensive washing with TBS containing 0.05 percent Tween-20, specifically bound material was eluted with the elution buffer, the pH immediately adjusted to 7.8 with 0.1 volume 1 M Tris-Hcl, pH 8.5, and stored at 4° C. The specific activity of this purified lymphotoxin was $2-10\times10^7$ units/mg, as measured in the above murine L-929 assay.

The eluate contained most of the activity loaded onto the column. The majority of the total eluate protein migrated as a single band under both reducing and non-reducing conditions in SDS-polyacrylamide gel electrophoresis. The mobility of this band corresponds to approximately 18,000 MW, which is consistent with the predicted value of 18,664 MW based on the deduced amino acid sequence. To further characterize its biological activities, the purified recombinant lymphotoxin was tested for cytolytic activity in vitro and antitumor activity in vivo.

EXAMPLE 5

In Vivo Biological Activity of Recombinant Lymphotoxin

Recombinant and lymphoblastoid lymphotoxin were tested in an in vivo tumor necrosis assay. MethA(a) sarcomas were grown for 7–10 days in susceptible mice [BALB/C×C57B1/6fl or CB6fl], and the tumors then directly injected with Example 4 lymphotoxin, lymphoblastoid lymphotoxin (prepared and purified as described above) or control samples After 20–24 hours, the mice were sacrificed, the tumors removed and histologically scored for the extent of necrosis. As shown in Table 1, both recombinant and lymphoblastoid lymphotoxin caused significant necrosis of MethA(a) sarcoma in vivo. Control samples did not induce necrosis of the MethA(a) sarcomas.

TABLE 1

NECROSIS OF MethA(a) SARCOMA IN VIVO BY RECOMBINANT AND NATURAL LYMPHOTOXIN

| Treatment | Number of Mice Sarcoma Necrosis Score +++ | ++ | + | − |
|---|---|---|---|---|
| Buffer 1 control | — | — | — | 3 |
| Lymphoblastoid Lymphotoxin, 25,000 units | 4 | — | — | — |
| Lymphoblastoid Lymphotoxin, 10,000 units | 4 | — | — | — |
| Recombinant Lymphotoxin, 200,000 units | 14 | 2 | 2 | — |
| Recombinant Lymphotoxin, 25,000 units | 3 | — | — | 1 |
| Recombinant Lymphotoxin, 10,000 units | 3 | — | 1 | — |
| Buffer 2 Control | — | — | — | 9 |

Lymphoblastoid lymphotoxin was injected dissolved in buffer 1 (0.01 M tris-HCl, 0.05 M $(NH_4)_2HCO_3$, pH 8.0) and recombinant lymphotoxin was injected dissolved in Buffer 2 (0.15 M NaCl, 0.1 M sodium acetate and 0.1 M Tris-HCl, pH 7.8).

The absence of carbohydrate on recombinant lymphotoxin does not appear to effect biological activity, since the specific activity of lymphotoxin produced by recombinant culture ($2-10\times10^7$ units/mg) is approximately the same as that reported for lymphoblastoid lymphotoxin ($4\times10^7$ units/mg).

The recombinant lymphotoxin activity also exhibited thermolability similar to natural lymphotoxin, i.e., inactivation in aqueous solution after heating for 1 hour at 80° C.

EXAMPLE 6

Construction of an Expression Vector for Methionyl Histidyl Amino-Terminal Lymphotoxin Construction of a plasmid which directs the expression of histidyl amino-terminal lymphotoxin is outlined in FIG. 3. A synthetic oligonucleotide was inserted into the expression plasmid so as to encode an initiator methionine codon adjadent to the histidyl codon of histidyl amino terminal lymphotoxin (residue 24 of FIG. 2*a*). This was performed by isolating a 4630 bp vector fragment from plTtrp1 by XbaI and ClaI digestion, preparative 1 percent agarose gel electrophoresis, and electroelution. A 570 bp BamHI-ClaI fragment containing most of the lymphotoxin coding sequence was also isolated from plTtrp1 in the same fashion. Two synthetic oligonucleotides were synthesized by methods discussed previously and mixed with oligonucleotides 6, 7, 52 and 53 of FIG. 1*a*. Approximately 50 pmol of each oligonucleotide was treated with polynucleotide kinase as described in Example 1. The oligonucleotides were annealed and then ligated with a mixture of the 570 bp BamHI-ClaI fragment and the 4630 bbp XbaI-ClaI vector fragment. The ligation mixture was transformed into *E. coli* ATCC 31446 and recombinants were selected on the basis of resistance to tetracycline. The resulting plasmid, p20KLT was characterized by DNA sequence analysis.

EXAMPLE 7

Procaryotic Secretion System for Lymphotoxin Free of Amino-Terminal Methionyl A plasmid which directs the expression of lymphotoxin secreted into the periplasmic space of *E. coli* was constructed by cloning a sequence coding for a bacterial signal sequence adjacent to the structural gene for lymphotoxin. The sequence of the gene for the heat-stable Enterotoxin II (STII) of *E. coli* has been characterized (R. N. Picken et al., 1983, "Infection and Immunity" 42: 269–275) and encodes a 23 amino acid signal sequence which directs the secretion of the STII into the periplasmic space. The STII gene has been engineered for expression in *E. coli* under trp control similar to that detailed for lymphotoxin (pLTtrp1 or p20KLT). The STII coding gene was cloned into the phage DNA M13mp8 (J. Messing et al., 1982, Gene 19:269–276) with the lymphotoxin gene from pLTtrp1 cloned downstream of the STII sequence. The sequence between the STII signal and the sequence coding for leucyl-amino terminal lymphotoxin (or histidyl amino-terminal lymphotoxin) was deleted by in vitro deletional mutagenesis (J. P. Adelman et al., 1983, "DNA" 2: 183–193). A recombinant containing the correct sequence (trp—ATG leucyl amino terminal lymphotoxin) was identified by hybridization and sequence analysis (designated pSTLT18). A similar construction was identified coding for histidyl amino-terminal lymphotoxin (designated pSTLT16). The mutagenized sequences were then isolated from the recombinant phage DNAs and cloned into trp expression plasmids (constructed like pLTtrp1 and p20KLT except that the mutagenized sequences contained the STII signal sequence). The resulting plasmids were transformed into *E. coli* ATCC 31446. *E. coli* containing the plasmid pSTLT18 secrete leucyl amino-terminal lymphotoxin into the periplasmic space and *E. coli* containing pSTLT16 secrete histidyl amino-terminal lymphotoxin into the periplasmic space.

EXAMPLE 8

Method for Making Monoclonal Murine Antibody Capable of Neutralizing Lymphotoxin Purified lymphoblastoid lymphotoxin obtained in Example 1 was dialyzed against phosphate buffered saline (PBS). 200 μg of lymphotoxin/ml were contained in the dialysate. Glutaraldehyde was added to the dialysate to a concentration of 70 mM glutaraldehyde, the mixture incubated for 2 hours at room temperature, more glutaraldehyde added to bring its total added concentration up to 140 mM, incubation continued for another 6 hours and the mixture then dialyzed against PBS. 50 μl of the glutaraldehyde cross-linked lymphotoxin (hereafter, "polylymphotoxin") and 0.5 ml of Freund's complete adjuvant was injected subcutaneously into mice (strain BALB/c). After one week, the mouse was booster immunized with 50 μg of polylymphotoxin and 0.5 ml of Freund's incomplete adjuvant, half intramuscularly and half into the peritoneal cavity. Serum was harvested after 7 days and assayed for anti-lymphotoxin activity by an ELISA assay.

The ELISA assay was conducted as follows: A buffered solution of purified lymphotoxin was placed in microtiter wells and permitted to coat the wells with about 100 ηg of lymphotoxin each. The unadsorbed lymphotoxin solution was aspirated from the wells. 50 μl of appropriately diluted test sample was combined with 100 μl PBS containing 5 mg/ml bovine serum albumin (PBS-BSA buffer) and added to each well, incubated for 2 hours at room temperature, washed with PBS containing 0.05 percent Tween 20, 100 μl of horse radish peroxidase-labelled goat anti-mouse IgG in PBS-BSA buffer added to each well and incubated for 1 hour. Each well was washed with PBS containing 0.05 percent Tween 20 and then citrate phosphate buffer, pH5, containing 0.1 mg o-phenylene diamine/ml (substrate solution) and aqueous 30 percent $H_2O_2$ (at a proportion of 4 μl of 30 percent $H_2O_2$ per 10 ml of substrate solution) was added to each well. The wells were incubated for 30 min., the reaction stopped with 50 μl 2.5M sulfuric acid and adsorbance measured at 492 nm. Wells which showed adsorbance greater than 1 O.D. were considered anti-lymphotoxin positive.

Test samples also were assayed for the ability to neutralize the cytolytic activity of lymphotoxin in the murine L929 assay. Serum harvested from immunized animals or hybridoma supernatants were diluted as required into RPMI-1640 medium containing 10 percent fetal bovine serum and about 100 lymphotoxin units/ml and plated into microtiter wells containing cultured L929 cells as is otherwise conventional in the cytolysis assay. In the control, all cells were lysed. Neutralizing antibody was detected by failure of the lymphotoxin to lyse L929 cells.

The animal immunized with glutaraldehyde-polymerized lymphotoxin raised antibodies which were active in the ELISA assay, but no serum neutralizing activity was detected.

A suspension containing 100 μg lymphotoxin and 1 ml of a 1.64 percent w/v suspension of aluminum hydroxide [$(Al(OH)_3$] was prepared and used to immunize the same mouse. The mouse was injected with 100 μl of the suspension intramuscularly and 400 μl intraperitoneally. After one week the mouse was injected intravenously with 10 μg of lymphoblastoid, unpolymerized and unadsorbed lymphotoxin in 100 μl of PBS. A test of 1/80 dilution of the animal's serum three days later indicated the presence lymphotoxin neutralizing antibody.

The spleen from this animal was harvested. $3\times10^7$ spleen cells were fused with $5\times10^7$ murine myeloma cells and plated into microtiter wells containing HAT medium and about 3000 peritone macrophages/microtiter well according to the procedure of S. Fazekas De St. Groth, 1980, "J. Immunol. Meth." 35: 1-21. Hybridomas from wells containing supernatants which were positive in the above ELISA assay were grown in 1 ml volume of DMEM medium with 20 percent fetal calf serum, 10 percent NCTC-135 medium, $5\times10^{-5}$ M beta-mercaptoethanol and HAT, distributed into microtiter wells at a statistical average of one cell per well and then cultured in a 1 or 5 ml volume of the same medium. Supernatants were assayed for neutralizing antibody after culture in each volume. Statistically, about 2 percent of the ELISA positive hybridomas from the aluminum hydroxide immunization synthesized neutralizing antibody. Lymphotoxin antibody secreting hybridomas were assayed for affinity in order to obtain an antibody exhibiting high affinity.

EXAMPLE 9

Site-Specific Mutagensis of LT

The method of Example 3 was followed exactly in this contemplated example except that segment 6 of the synthetic oligonucleotide was modified to have the sequence 5'CTCAACTCTGCACCCA3' and its complementary strand (segment 53) modified to have the sequence 3'AGACGTGGGTCGTCGT5'.

The modified oligonucleotides were annealed to the remaining oligonucleotides and ligated into the expression vector as described in Example 6. This vector contained a 2 bp substitution which changed the lysine +28 codon from lysine to histidine. The histidine mutant could be expressed upon transformation and culture of *E. coli*.

I claim:

1. An anti-lymphotoxin monoclonal antibody which neutralizes the cytolytic activity of a lymphotoxin having the amino acid sequence Leu-Pro-Gly-Val-Gly-Leu-Thr-Pro-Ser-Ala-Gln-Thr-Ala-Arg-Gln-His-Pro-Lys-Met-His-Leu-Ala-His-Ser-Thr-Leu-Lys-Pro-Ala-Ala-His-Leu-Ile-Gly-Asp-Pro-Ser-Lys-Gln-Asn-Ser-Leu-Leu-Trp-Arg-Ala-Asn-Thr-Asp-Arg-Ala-Phe-Leu-Gln-Asp-Gly-Phe-Ser-Leu-Ser-Asn-Asn-Ser-Leu-Leu-Val-Pro-Thr-Ser-Gly-Ile-Tyr-Phe-Val-Tyr-Ser-Gln-Val-Val-Phe-Ser-Gly-Lys-Ala-Tyr-Ser-Pro-Lys-Ala-Thr-Ser-Ser-Pro-Leu-Tyr-Leu-Ala-His-Glu-Val-Gln-Leu-Phe-Ser-Ser-Gln-Tyr-Pro-Phe-His-Val-Pro-Leu-Leu-Ser-Ser-Gln-Lys-Met-Val-Tyr-Pro-Gly-Leu-Gln-Glu-Pro-Trp-Leu-His-Ser-Met-Tyr-His-Gly-Ala-Ala-Phe-Gln-Leu-Thr-Gln-Gly-Asp-Gln-Leu-Ser-Thr-His-Thr-Asp-Gly-Ile-Pro-His-Leu-Val-Leu-Ser-Pro-Ser-Thr-Val-Phe-Phe-Gly-Ala-Phe-Ala-Leu and which is free of non-neutralizing antibodies.

2. The antibody of claim 1 which is immobilized on a surface or matrix.

3. A method for separating lymphotoxin from a composition, which method comprises immobilizing on a surface or matrix the anti-lymphotoxin antibody of claim 1, contacting the immobilized antibody with the composition under conditions whereby lymphotoxin is absorbed thereon, separating the antibody-absorbed lymphotoxin from the composition and separating the lymphotoxin from the antibody.

4. The antibody of claim 1 which is labelled with a detectable substance from the group of fluorescent, chemiluminescent or radioisotopic labels.

* * * * *